United States Patent [19]

Smith et al.

[11] Patent Number: 5,082,600

[45] Date of Patent: * Jan. 21, 1992

[54] TRANSPARENT SOAP BAR PROCESS USING TRIALKYLAMINE OXIDE DIHYDRATE

[75] Inventors: Kim R. Smith; James E. Borland, both of Baton Rouge, La.

[73] Assignee: Ethyl Corporation, Richmond, Va.

[*] Notice: The portion of the term of this patent subsequent to Oct. 8, 2008 has been disclaimed.

[21] Appl. No.: 416,113

[22] Filed: Oct. 2, 1989

Related U.S. Application Data

[63] Continuation-in-part of Ser. No. 344,275, Apr. 26, 1989, abandoned.

[51] Int. Cl.⁵ .................... C11D 1/75; C11D 17/00
[52] U.S. Cl. ................... 252/547; 252/117; 252/134; 252/132; 252/DIG. 16; 252/174
[58] Field of Search ............ 252/110, 122, 117, 118, 252/132, 134, 122, 174, DIG. 16, 547

[56] References Cited

U.S. PATENT DOCUMENTS

| | | | |
|---|---|---|---|
| 3,202,714 | 8/1965 | Zimmerer et al. | 252/547 |
| 3,223,647 | 12/1965 | Drew et al. | 252/117 |
| 3,926,828 | 12/1975 | O'Neill et al. | 252/118 |
| 4,206,069 | 6/1980 | Borrello | 252/122 |
| 4,320,033 | 3/1982 | Yoshikawa | 252/547 |
| 4,960,934 | 10/1990 | Smith et al. | 546/192 |

*Primary Examiner*—David L. Lacey
*Assistant Examiner*—Thomas E. Daley
*Attorney, Agent, or Firm*—Joseph D. Odenweller; Patricia J. Hogan

[57] ABSTRACT

Transparent soap bars are made by a process comprising mixing solid, non-hydroscopic trialkylamine oxide dihydrate with a fatty acid soap and other conventional ingredients such as triethanolamine, glycerine, water, perfume, and the like.

11 Claims, No Drawings

TRANSPARENT SOAP BAR PROCESS USING TRIALKYLAMINE OXIDE DIHYDRATE

PRIOR APPLICATION

This application is a continuation-in-part of Application Ser. No. 344,275, filed Apr. 26, 1989, now abandoned.

BACKGROUND

Transparent soap bars have been on the market for many years. They are considered aesthetically pleasing to the eye. They are generally defined as having sufficient transparency so that fourteen point type can be read through a one-quarter inch thick bar. When properly formulated, they are quite mild but are somewhat deficient in hard water properties. Furthermore, they are fairly soft due to their water content and have poor slough properties. Typical transparent soap bars are described in Kamen U.S. Pat. No. 3,562,167, Jungermann et al. U.S. Pat. No. 4,758,370, and Poper et al. U.S. Pat. No. 4,290,904, which are incorporated herein by reference.

It has been suggested to use alkyl dimethylamine oxides in transparent detergent bars because of their excellent foaming properties (cf. Poper et al. U.S. Pat. No. 4,290,904). However, a satisfactory way of doing this on a commercial scale has not been developed. The problem is that alkyl dimethylamine oxides (e.g., dodecyl dimethylamine oxide) are made by reacting aqueous hydrogen peroxide to form an aqueous solution of the alkyl dimethylamine oxide. In practice it has been reported that such solutions should not exceed about 30 weight percent active alkyl dimethylamine oxides or the solution will form an unstirrable gel preventing completion of this reaction. Commercially lauryl dimethylamine oxide is sold as a 30 weight percent aqueous solution. Use of this 30 weight percent solution of alkyl dimethylamine oxide in formulating a soap bar leads to the introduction of an excessive amount of water into the soap bar. For example, if this bar is formulated to contain 10 weight percent alkyl dimethylamine oxide, it will of necessity contain at least 23.3 weight percent water. Such high water levels lead to a very soft soap bar with an unacceptable slough rate. On the laboratory scale this problem appears to have been circumvented by distilling this water from the alkyl dimethylamine oxide solution to form an anhydrous alkyldimethylamine oxide which can be used in the laboratory preparation of a soap bar as shown in Poper et al. U. S. Pat. No. 4,290,904. However, it is impractical to convert 30 weight percent aqueous solutions of alkyl dimethylamine oxides to a dry product on a commercial scale because of the large amount of water involved. Hence, a need exists for an efficient method of making transparent soap bars which contain an effective amount of alkyl dimethylamine oxide without introducing an excessive amount of water and without the need to perform the arduous removal of water from the commercial alkyldimethylamine oxide solution.

SUMMARY

According to the present invention, transparent soap bars which contain effective amounts of alkyl dimethylamine oxides and which possess excellent slough characteristics can be made by mixing a non-hygroscopic alkyl dimethylamine oxide dihydrate with a fatty acid soap and other ingredients conventionally used in transparent soap bars.

DESCRIPTION OF THE PREFERRED EMBODIMENTS

A preferred embodiment of this invention is a method of making a transparent soap bar, said method comprising mixing (i) a non-hygroscopic trialkylamine oxide dihydrate having the structure:

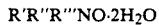

wherein R' is a primary alkyl containing 8-24 carbon atoms, R" is methyl, ethyl or a primary alkyl containing 8-24 carbon atoms and R''' is methyl or ethyl, and (ii) a fatty acid soap and optionally other conventional transparent soap bar ingredients, the amount of said trialkylamine oxide dihydrate being sufficient to comprise 1-25 weight percent of the resultant transparent soap bar.

The essential trialkylamine oxide dihydrates can be made by the process described in Application Ser. No. 344,275, filed Apr. 26, 1989. According to this process, the appropriate amine is reacted with at least a stoichiometric amount of concentrated (e.g., 50-70 weight percent active) hydrogen peroxide in an organic ester solvent (e.g., ethyl acetate) in an amount sufficient to maintain a fluid reaction mixture. Reaction temperatures of about 25-100° C. can be used. A preferred range is 60-75° C. Carbon dioxide can be injected to promote the reaction. Use of about 1.2 theories of 70 weight percent hydrogen peroxide results in a final reaction mixture which contains about 2 moles of water per mole of amine oxide. If more water than this is present, it should be distilled out to obtain a 2/1 water/amine oxide mole ratio. The organic ester solution can then be cooled causing the amine oxide dihydrate to crystallize. Alternatively, the organic ester can be distilled out at atmospheric pressure or under vacuum to obtain the amine oxide dihydrate as the residue. It was surprisingly found that the tert-amine oxide dihydrate was not hygroscopic.

Trialkylamines useful in making the tert-amine oxide dihydrate are those having the formula R'R"R'''N wherein R', R" and R''' are as previously defined. Representative examples of these are:

n-octyl diethylamine
n-decyl dimethylamine
n-decyl diethylamine
n-dodecyl dimethylamine
n-dodecyl diethylamine
n-tetradecyl dimethylamine
n-hexadecyl diethylamine
n-octadecyl dimethylamine
n-eicosyl dimethylamine
di-(n-octyl)methylamine
di-(n-decyl)methylamine
di-(n-dodecyl)ethylamine
di-(n-tetradecyl)methylamine
di-(n-hexadecyl)ethylamine
di-(n-octadecyl)methylamine
di-(n-eicosyl)methylamine
n-octyl n-dodecyl methylamine
n-decyl n-octadecyl ethylamine
n-decyl n-eicosyl ethylamine and the like including mixtures thereof.

Of the above, a still more preferred class of tertamines consists of those in which R' is a $C_{8-24}$ primary alkyl, R" is methyl or a $C_{8-24}$ primary alkyl and R''' is methyl. Examples of these are:

octyl dimethylamine
decyl dimethylamine
dodecyl dimethylamine
tetradecyl dimethylamine
hexadecyl dimethylamine
eicosyl dimethylamine
docosyl dimethylamine
tetracosyl dimethylamine
dioctyl methylamine
didecyl methylamine
didodecyl methylamine
decyl dodecyl methylamine
ditetradecyl methylamine
tetradecyl octyl methylamine and the like including mixtures thereof.

The following Examples show how to make the required trialkylamine oxide dihydrate.

EXAMPLE 1

In a 250 milliliter glass reaction flask was placed 100 grams of tetradecyldimethylamine (0.41 mole; amine value 230.0 mg KOH/g amine) and 0.5 gram (1.27 mmol) of diethylenetriaminepentaacetic acid. This was heated with stirring to 65 C and then 23 grams (0.47 mole) of 70 weight percent aqueous hydrogen peroxide was added dropwise over a 15-minute period. The mixture was then heated to 76° C. and stirred at that temperature for seven hours. As needed, ethyl acetate (34 mL) was added dropwise to the reaction mass in order to maintain a clear, gel-free liquid. Analysis of the crude reaction mass showed 99 percent amine conversion by proton NMR. The crude reaction mass was added to 400 mL additional ethyl acetate. The solution was then cooled to 15° C. forming a non-hydroscopic white crystalline solid tetradecyldimethylamine oxide dihydrate in 86% recovered yield melting at about 41° C.

EXAMPLE 2

In a glass reaction flask was placed 100 g tetradecyl dimethylamine and 0.5 g diethylenetriamine pentaacetic acid. Carbon dioxide sparge into the liquid phase was started and the mixture was stirred and heated to 65° C. The $CO_2$ sparge was stopped and a $CO_2$ gas phase was maintained over the reaction mixture. Dropwise feed of 70 weight percent aqueous hydrogen peroxide was started. At the same time, addition of ethyl acetate was commenced. After 10 minutes all the hydrogen peroxide and 28 mL of ethyl acetate had been added. Cooling was required to maintain the temperature under 75° C. Heat was applied and the reaction continued for two more hours. Dropwise addition of ethyl acetate was continued for the first 19 minutes of the two-hour period. Total ethyl acetate feed was 43 mL. The reaction mixture was a clear gel-free solution. The reaction mixture was analyzed by NMR showing a 100 percent amine conversion. The reaction mixture was poured into a flask containing 400 mL of ethyl acetate and cooled to 15 C. Needle-like crystals of tetradecyl dimethylamine oxide dihydrate form (106 g) indicating a 87 percent yield.

The amount of the trialkylamine oxide dihydrate in the transparent bar can vary from about 1-25 weight percent. A preferred amount is about 3-15 weight percent and most preferably 5-10 weight percent.

Other ingredients in the transparent bar include at least one fatty acid soap. These include the sodium and/or amine salts of $C_{12}-C_{20}$ fatty acids, especially stearic ricinoleic acid, coco fatty acid, tallow fatty acid mixtures, and oleic acid. Suitable amines include ethanol amine, diethanol amine, and triethanol amine. The amount of fatty acid soap ranges from about 50-90 weight percent.

Other conventional surfactants can optionally be included in these formulations but are not essential. These include sodium laurylsulfates, triethanolamine laurylsulfate, lauroyl sarcosine, nonylphenol ethoxylate (9).

Glycerol is co-produced in the saponification of tallow and is generally included as a minor component, up to about 25 weight percent, in the formulated bar. Likewise, other polyols such are ethylene glycol, propylene glycol, polyethylene glycol.

In the past it has not been practical to include trialkylamine oxides in toilet detergent bar formulations because such trialkylamine oxides are made in an aqueous solution to avoid gel formation. Solutions containing in excess of about 30 weight percent $C_{8-24}$ alkyl dimethylamine oxide tend to gel. This prevents stirring of the reaction mixture. Use of the commercially available 30 percent alkyl dimethylamine oxide aqueous solutions in the process of making detergent bars introduces an excessive amount of water forming an unacceptably soft bar. The only way around this problem in the past appears to have been to distill out all the water from the trialkylamine oxide solution forming an anhydrous trialkylamine oxide. This is only useful on the laboratory scale.

In the process of the present invention, the detergent bar is made by mixing a defined trialkylamine oxide dihydrate with the other components used to formulate the detergent bar. The lower carbon number dihydrates are liquids. For example, octyl dimethylamine oxide dihydrate melts at about 15° C. The more preferred $C_{12-24}$ alkyl dimethylamine oxide dihydrates are initially solids when made. For example, dodecyldimethylamine oxide dihydrate melts at about 30 C and octadecyldimethylamine oxide dihydrate melts at about 62° C. They may be produced in flaked, crystalline or drum cast form. The flaked and crystalline material may be readily added to the mixing vessel as a solid. If it is preferred to handle liquid materials the dihydrates may be heated to form a molten product and added to the mixing unit as a liquid. Such trialkylamine oxide dihydrates have been found to be non-hygroscopic and can be readily mixed with other components used to make a useful detergent bar without introducing an excessive amount of water. The trialkylamine oxide dihydrates can be made by the process described in our earlier U. S. Patent Application Ser. No. 344,275, filed Apr. 26, 1989, now abandoned.

The present method of making a transparent detergent bar is shown in the following Example.

EXAMPLE 3

In a mixing vessel was placed 5.5 pph (parts by weight per 100 parts final blend) crystalline n-tetradecyl dimethylamine oxide dihydrate, 34 pph of sodium salt of a 80/20 mixture of tallow and coco fatty acids, 34. pph triethanolamine, 10 pph stearic acid and 16.5 pph water. The mixture was warmed to about 70-80° C. and the molten mixture stirred until homogeneous. It was then poured into soap bar molds and cooled to form clear, transparent light yellow sap bars. The bar had a pH of 9 in water.

The soap bar was subjected to an industry-standard foam test. In this test, 30 mL of a 0.1 weight percent aqueous solution of the test soap bar is placed in a 100 mL graduate. The graduate is stoppered and rotated end-over-end ten times. The initial foam volume (referred to as "flash foam") is measured. The foam is measured a second time after 5 minutes as an indication of foam stability. The test detergent bar made by the present process had a flash foam of 7 mL and a 5-minute foam of 6 mL in soft water. In hard water (2000 ppm as $CaCO_3$) the flash foam was 5 mL and the 5-minute foam was 2 mL. Washing with the bar made by the present process left a smooth and moist skin feel.

We claim:

1. A method of making a transparent soap bar, said method comprising mixing (i) a non-hygroscopic trialkylamine oxide dihydrate having the structure:

$$R'R''R'''N O \cdot 2H_2O$$

wherein R' is a primary alkyl containing 8-24 carbon atoms, R'' is methyl, ethyl or a primary alkyl containing 8-24 carbon atoms and R''' is methyl or ethyl, and (ii) a fatty acid soap and optionally other conventional transparent soap bar ingredients, the amount of said trialkylamine oxide dihydrate being sufficient to comprise 1-25 weight percent of the resultant transparent soap bar.

2. A method of claim 1 wherein R' and R'' are primary mainly linear alkyls containing 8-24 carbon atoms and R''' is methyl.
3. A method of claim 2 wherein R' and R'' are decyl.
4. A method of claim 1 wherein R' is a primary mainly linear alkyl containing 8-24 carbon atoms and R'' and R''' are methyl.
5. A method of claim 4 wherein R' is dodecyl.
6. A method of claim 4 wherein R' is tetradecyl.
7. A method of claim 4 wherein R' is hexadecyl.
8. A method of claim 4 wherein R' is octadecyl.
9. A method of claim 4 wherein R' is eicosyl.
10. A method of claim 4 for making a transparent soap bar, said method comprising mixing:
    (a) 1-25 weight percent $C_{12-24}$ alkyl dimethylamine oxide dihydrate
    (b) 20-50 weight percent fatty acid soap
    (c) 20-50 weight percent triethanol amine
    (d) 5-50 weight percent stearic acid
    (e) 10-20 weight percent water in amounts such that the total does not exceed 100 percent.
11. A method of claim 10 wherein said $C_{12-24}$ alkyl dimethylamine oxide dihydrate is tetradecyl dimethylamine oxide dihydrate.

* * * * *